US007448144B2

(12) United States Patent
Johnson et al.

(10) Patent No.: US 7,448,144 B2
(45) Date of Patent: Nov. 11, 2008

(54) AIR TREATMENT DEVICE FOR AGRICULTURAL BUILDINGS

(76) Inventors: Matthew W. Johnson, 1890 Red Leaf Ct., Windom, MN (US) 56101; Dennis J. Johnson, 1890 Red Leaf Ct., Windom, MN (US) 56101

( * ) Notice: Subject to any disclaimer, the term of this patent is extended or adjusted under 35 U.S.C. 154(b) by 313 days.

(21) Appl. No.: 11/216,939

(22) Filed: Aug. 31, 2005

(65) Prior Publication Data

US 2007/0044339 A1    Mar. 1, 2007

(51) Int. Cl.
F26B 21/06 (2006.01)
(52) U.S. Cl. ............... 34/80; 34/79; 96/152; 435/290.1
(58) Field of Classification Search .................. 34/218, 34/226, 227, 79, 80, 81, DIG. 1; 435/236, 435/290.1, 290.4
See application file for complete search history.

(56) References Cited

U.S. PATENT DOCUMENTS

| | | | |
|---|---|---|---|
| 1,716,479 A | 5/1929 | Bilsky | |
| 1,716,481 A | 6/1929 | Bilsky | |
| 1,769,072 A | 7/1930 | Raney | |
| 3,556,734 A | 1/1971 | Peterson | |
| 3,888,642 A | 6/1975 | Toyama | |
| 4,666,854 A * | 5/1987 | Sugiura | ................... 435/290.4 |
| 5,000,768 A * | 3/1991 | Hwang | ........................ 55/308 |
| 5,427,610 A | 6/1995 | Croker | |
| 6,071,479 A | 6/2000 | Marra et al. | |
| 6,475,382 B2 | 11/2002 | Parent | |

FOREIGN PATENT DOCUMENTS

| | | |
|---|---|---|
| JP | 60-147217 | 8/1985 |
| JP | 60-153916 | 8/1985 |
| JP | 04-169721 | 6/1992 |

OTHER PUBLICATIONS http://www.geosynthetica.net/specifications/sewing_geotextiles.asp, "Sewing Geotextiles," geosynthetica website.
http://www.novaweld.com,Novaweld website.
"Livestock and Poultry Odor Workshop I," University of Minnesota, Dept. of Biosystems and Agricultural Eng., p. 47-60; 70-76; and 101-104 (1999).
"A Summary of Livestock Odor Research at the University of Minnesota 1995-1999," University of Minnesota, Dept. of Biosystems and Agricultural Eng. (Draft), p. A.1, A.3, A.9-A.14 (Oct. 21, 1999).

(Continued)

*Primary Examiner*—Kenneth B Rinehart
(74) *Attorney, Agent, or Firm*—Faegre & Benson LLP (57) ABSTRACT

An apparatus for treating air from an exhaust port of a building. The apparatus includes an enclosed pathway having an inlet for communication with an exhaust port, a discharge outlet, and a non-linear pathway portion between the inlet and discharge outlet. The non-linear pathway includes air treatment material positioned in communication with a portion of the pathway to expose the air to the air treatment material as it moves through the pathway. The apparatus includes an irrigation system for maintaining the moisture content of the air treatment material.

1 Claim, 7 Drawing Sheets

OTHER PUBLICATIONS

Jacobson, L. et al., "Odor Control for Animal Agriculture,"BEAU-17.1, p. B.1, B.3, B.5 and B.7, (Nov. 1998, revised Feb. 2000).

"Treatment Processes Workshop, Part I, Waste Characteristics and Odors," University of Minnesota, p. 1-8 (Feb. 1999).

"Treatment Processes Workshop, Part II, Principles of Microbiology and Biochemistry in Swine Manure Odor Production," University of Minnesota, p. 15-54 (Feb. 1999).

"Treatment Processes Workshop, Odor Control," University of Minnesota, p. 100-116 (Feb. 1999).

* cited by examiner

AIR TREATMENT DEVICE FOR AGRICULTURAL BUILDINGS

FIELD OF THE INVENTION

The present invention relates generally to the field of odor control in agricultural applications. More particularly, the invention relates to structures for reducing or controlling emissions of odorous gases from agricultural buildings or other similar structures.

BACKGROUND OF THE INVENTION

Unwanted by-products of producing livestock include the inherent odors, particularly those created by livestock waste. Livestock waste emits foul and noxious gases, including hydrogen sulfide and ammonia. Not only are these gases unpleasant and potentially dangerous for those who are located near waste collection areas, but many regulatory bodies regulate the permitted emissions of certain gases from an agricultural operation. Further, some regulatory bodies require larger agricultural operations to provide air emission plans, which include methods and practices that will be employed by the agricultural operations to minimize emissions of certain gases and procedures to respond to complaints directed at the facility, including identifying strategies to address the sources of odors and noxious gases. Compounding the problem is that agricultural businesses are often subjected to difficult market conditions, requiring that the livestock producer hold down costs.

Various strategies can be employed to reduce emissions. One alternative, described in U.S. patent application Ser. No. 11/155,669, incorporated herein by reference in its entirety, is to suppress or neutralize odors within a manure pit of an agricultural building. While this alternative works to suppress odors beneath the building, the odorous gases may also still need to be evacuated at some point in the future.

Another approach is to attempt to filter gases from exhaust air after it has been evacuated from the building. One known approach is to employ so-called biofilter materials as a filtration media. Biofiltration employs microorganisms present within biodegradable materials to break down gaseous contaminants and reduce the amount of hydrogen sulfide and ammonia present in exhaust air. Prior approaches port exhaust air from an agricultural building into an air plenum located below a field of biofilter material. As the exhaust air is forced into the plenum, the resulting pressure forces the air through the field. However, forcing air through a thick field of biofilter material creates head loss on the exhaust fan, resulting in a need for more a powerful exhaust fan. Further, a number of other factors, including the particular choice of biofilter material and the settling of biofilter material over time can exacerbate the head loss. In addition, a phenomenon known as channeling, which is the shifting of material across the field, can create localized areas within the field with reduced humidity as more air passes through areas with a smaller concentration of material. Reduced humidity can result in reduced microorganism activity, which unfortunately reduces the filtering capability of the field. In addition, it is recommended that biofilter fields be located on sloping, well-drained land to control the amount of moisture the field of biofilter material, thereby limiting where biofilter fields can be employed.

What is needed then, is an effective way to reduce the emission levels of odorous and noxious gases of exhaust air from agricultural applications, such as the exhaust air from agricultural livestock buildings. The solution should result in minimal head loss on the exhaust fan, be easily maintained, employable in a large number of applications, and should be relatively inexpensive.

SUMMARY OF THE INVENTION

One embodiment of the invention is an apparatus for treating air from an exhaust port of a building. The apparatus includes an enclosed pathway for connection to the exhaust port of the building and a non-linear pathway extending from the inlet to a discharge outlet. The apparatus further includes air treatment material positioned along at least a portion of the pathway so that air is exposed to the air treatment material as it moves through the pathway. Yet another embodiment of the invention includes an irrigation system for increasing the moisture content of the air treatment material. The irrigation system can include an inlet to be connected to a moisture source and at least one moisture distribution member such as a sprinkler for irrigating the air treatment material. The irrigation system further includes a flow control member that controls the flow of moisture from the moisture source to the at least one moisture distribution member. The irrigation system also includes a moisture sensing device positioned within the pathway. The moisture sensing device is coupled to a controller, which is also coupled to the flow control member to controlling the flow of moisture to the air treatment material.

DETAILED DESCRIPTION OF THE INVENTION

Figure 1:
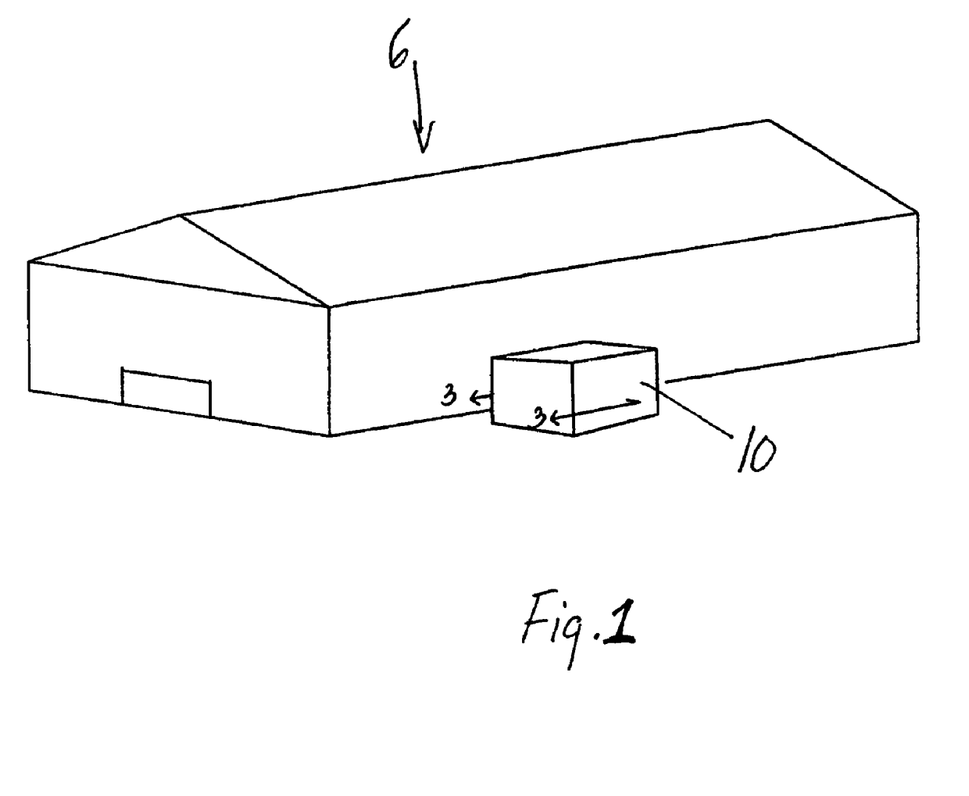
FIG. 1 is an isometric illustration of an agricultural building having an exhaust fan outlet coupled to an exhaust treatment member in accordance with one embodiment of the invention.
Figure 2:
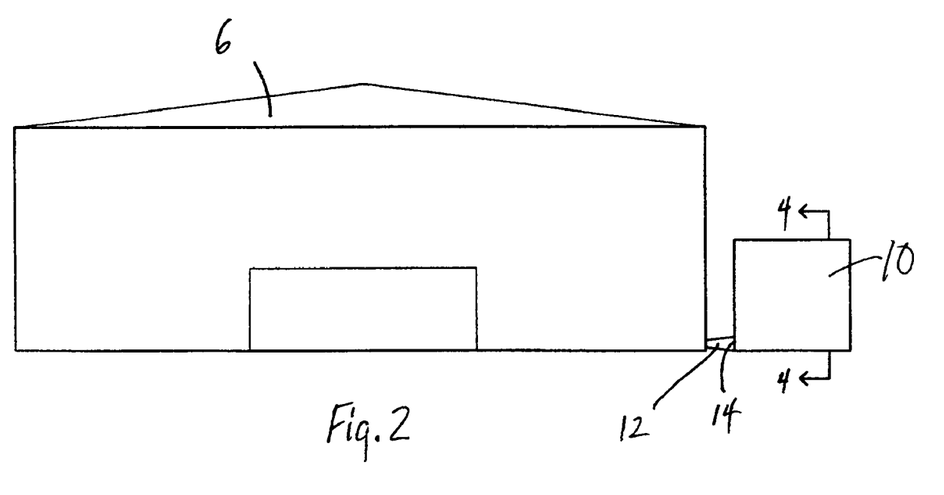
FIG. 2 is a front view of the agricultural building of FIG. 1, illustrating the coupling of the agricultural building to the exhaust treatment member.

FIGS. 1 and 2 illustrate an agricultural building 6 that is coupled to an exhaust treatment member 10 in accordance with one embodiment of the invention. The agricultural building 6 is coupled to the exhaust treatment member 10 on the output side of an exhaust fan (not shown) that is positioned to draw air out of the agricultural building. The exhaust fan is positioned near a manure pit (not shown) to evacuate air in the manure pit area, although the exhaust fan may be located anywhere as long as it can draw air out of the agricultural building 6. The agricultural building 6 is coupled to a treatment member inlet 14 on the exhaust treatment member 10 through a duct 12. Duct 12 has an interior cross section that is approximately the same or larger than an output port (not shown) on the output side of the exhaust fan at the location where output port is coupled to the duct 12. The interior cross sectional area of duct 12 is generally constant or increasing from the output port to the treatment member inlet 14.

Exhaust air from the barn 6 is thus forced through the exhaust output port and into the exhaust treatment member 10 through the treatment member inlet 14 to accommodate the air flow from the exhaust fan without creating a load on the exhaust fan. In addition, the duct 12 is shaped to mate with the treatment member inlet 14, which may have a different general shape than the exhaust port on the agricultural building 6. For example, the output port (not shown), in one embodiment, has a circular shape and the treatment member inlet 14 has a generally rectangular shape.

Figure 3:
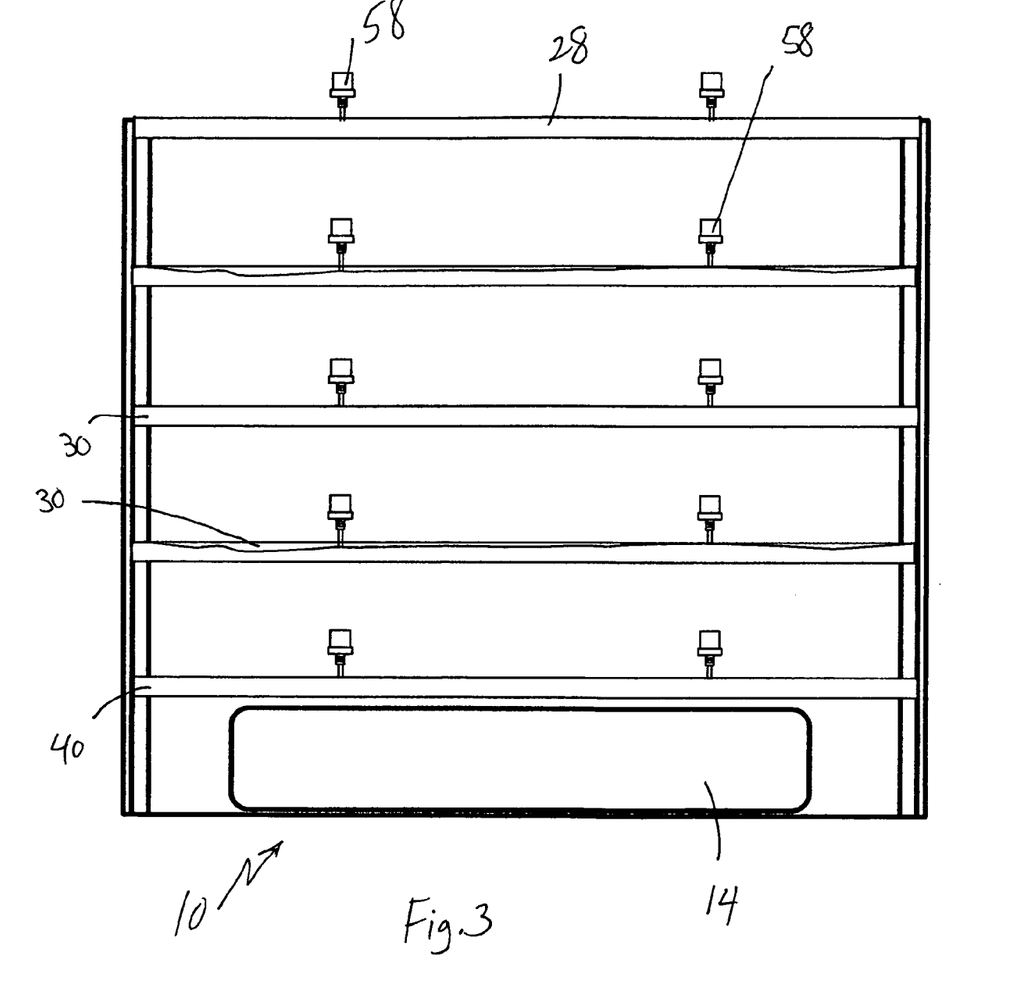
FIG. 3 is a cross sectional view through the exhaust treatment member along lines 3-3 in FIG. 1.
Figure 4:
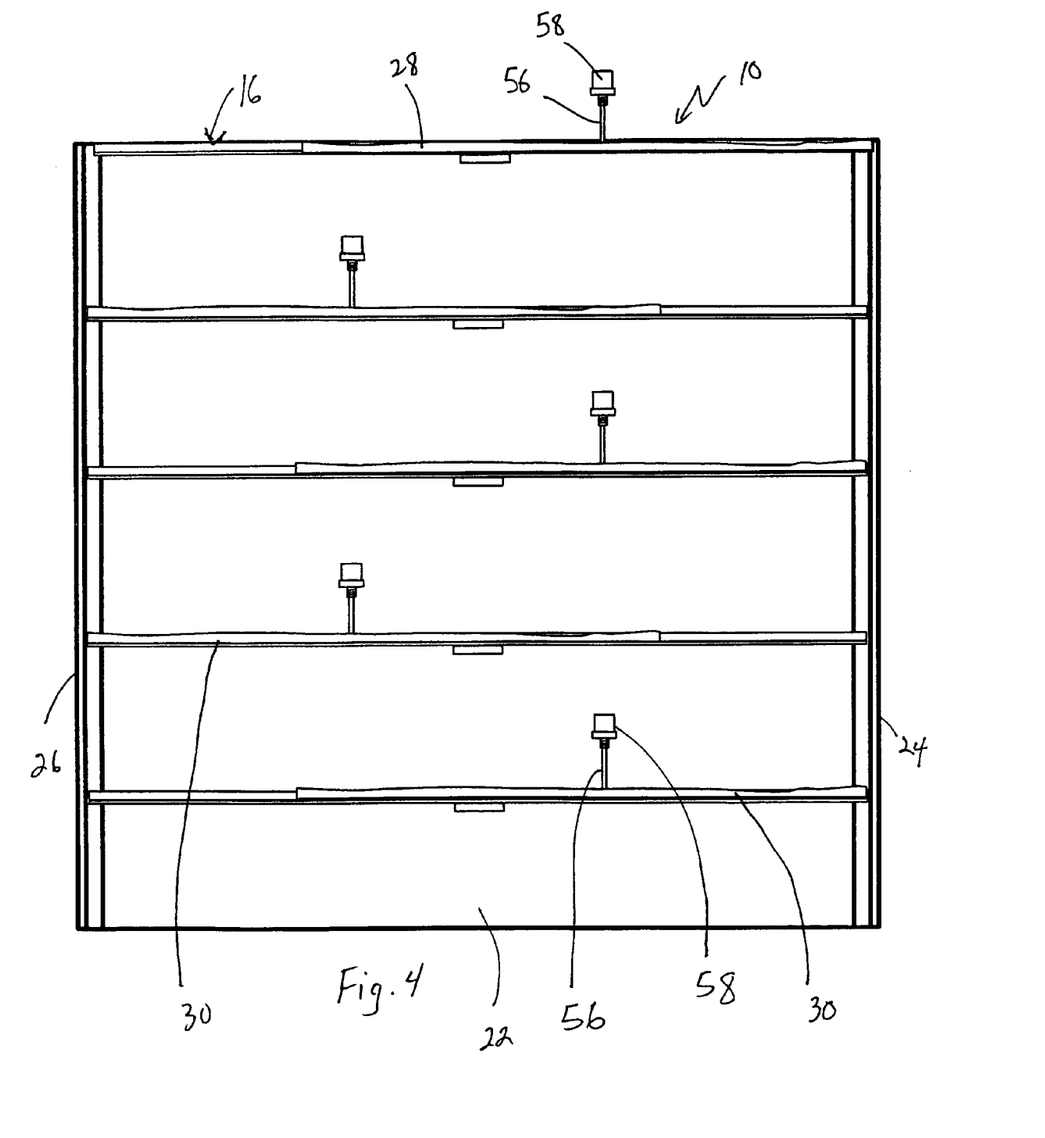
FIG. 4 is a cross sectional view through the exhaust treatment member along lines 4-4 in FIG. 2.
Figure 5:
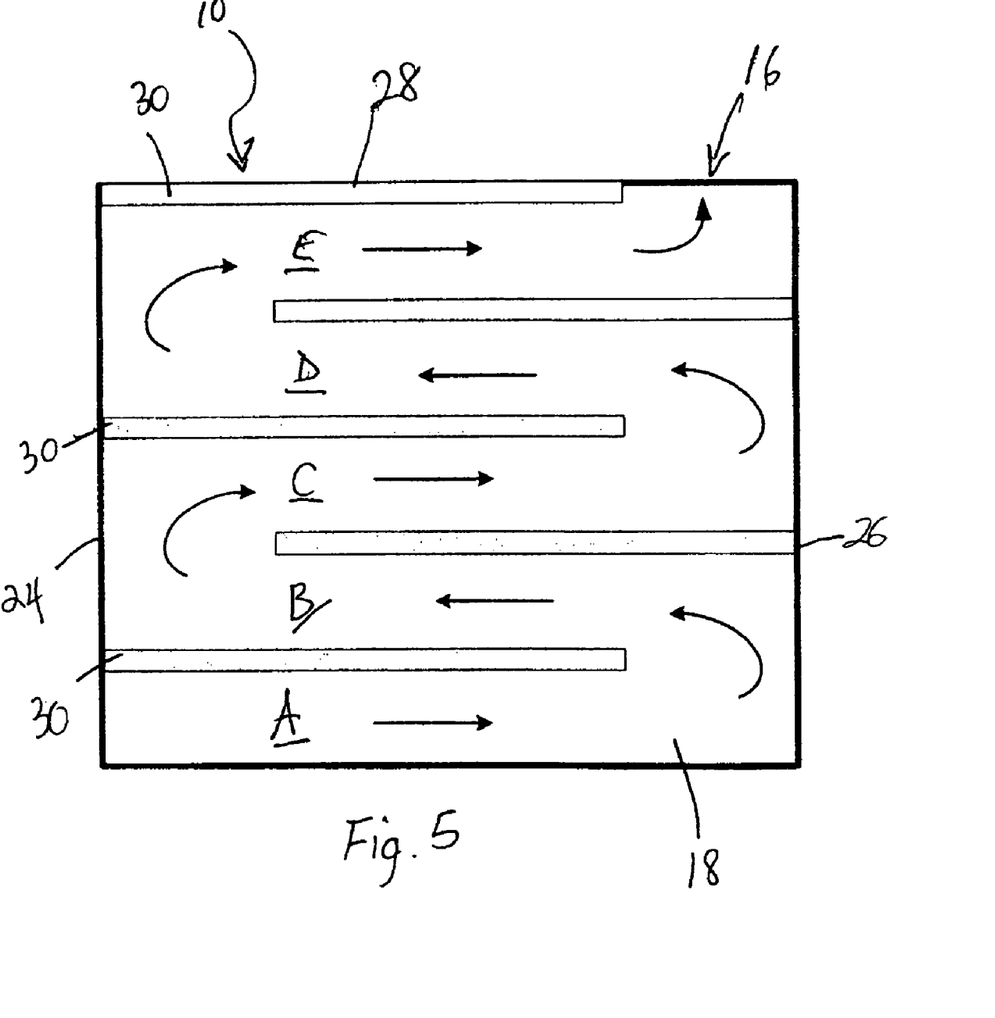
FIG. 5 is a schematic illustration of the air flow through the exhaust treatment member of FIG. 1.

Referring to FIGS. 3, 4, and 5, the exhaust treatment member 10, in one embodiment, is a generally rectangularly shaped structure with a generally hollow interior. The exhaust treatment member 10 includes a frame 20 and outer surfaces 22 attached to the frame 20. The frame 20 and outer surfaces 22 of exhaust treatment member 10 can be made of a number of known materials. For example, the frame and outer surfaces can be made of wood, metal, plastic, foam, or other suitable materials. The outer surfaces 22 preferably have some insulative properties to maintain warmth and, correspondingly, increased microorganism activity within the exhaust treatment member 10 during cold weather.

The interior of exhaust treatment member 10 includes a plurality of trays 30, adapted to hold an air treatment material 40, that are arranged within the exhaust treatment member 10. As illustrated in FIG. 3, the trays 30 have a width that is approximately the same as that of the exhaust treatment member 10. However, as illustrated in FIG. 4, the trays 30, have a length that is less than that of the exhaust treatment member 10. Further, the trays 30 are arranged within the housing so that the trays are alternately adjacent to a first side 24 and a second side 26, thereby creating a serpentine pathway 18, as shown in FIG. 5, for incoming air to make several turns as it moves through a plurality of segments A-E in the exhaust treatment member 10 from the treatment member inlet 14 to a discharge outlet 16. As the exhaust air moves through the pathway 18, it passes by each of the plurality of trays 30 with air treatment material 40. In one embodiment, five trays 30 are aligned within the exhaust treatment member 10, although any number of trays may be used as necessary. The trays 30 are arranged and sized within the exhaust treatment member 10 to define the pathway 18 with sufficient cross-sectional area to allow air to flow through exhaust treatment member 10 and interact with air treatment material 40 while creating minimal head loss on the exhaust fan.

A top surface 28, in the illustrated embodiment, is formed by a tray 30. Alternatively, a roof structure (not shown) is attached to the exhaust treatment member 10 to extend above the tray on the top surface 28 of the exhaust treatment member. Alternatively, the roof extends above the entire top surface 28 and the discharge outlet 16 is channeled out of the exhaust treatment member 10 beneath the roof. Alternatively still, the tray 30 that forms the top surface 28 may extend across the entire top surface, including the exhaust port (not shown). As the exhaust air passes through the serpentine pathway 18 it will gradually decrease in velocity even as it interacts with the material in the trays 30. In addition the final tray has a relatively small amount of treatment material located within it, so that the exhaust air can pass through it with minimal head loss on the fan.

Figure 6:
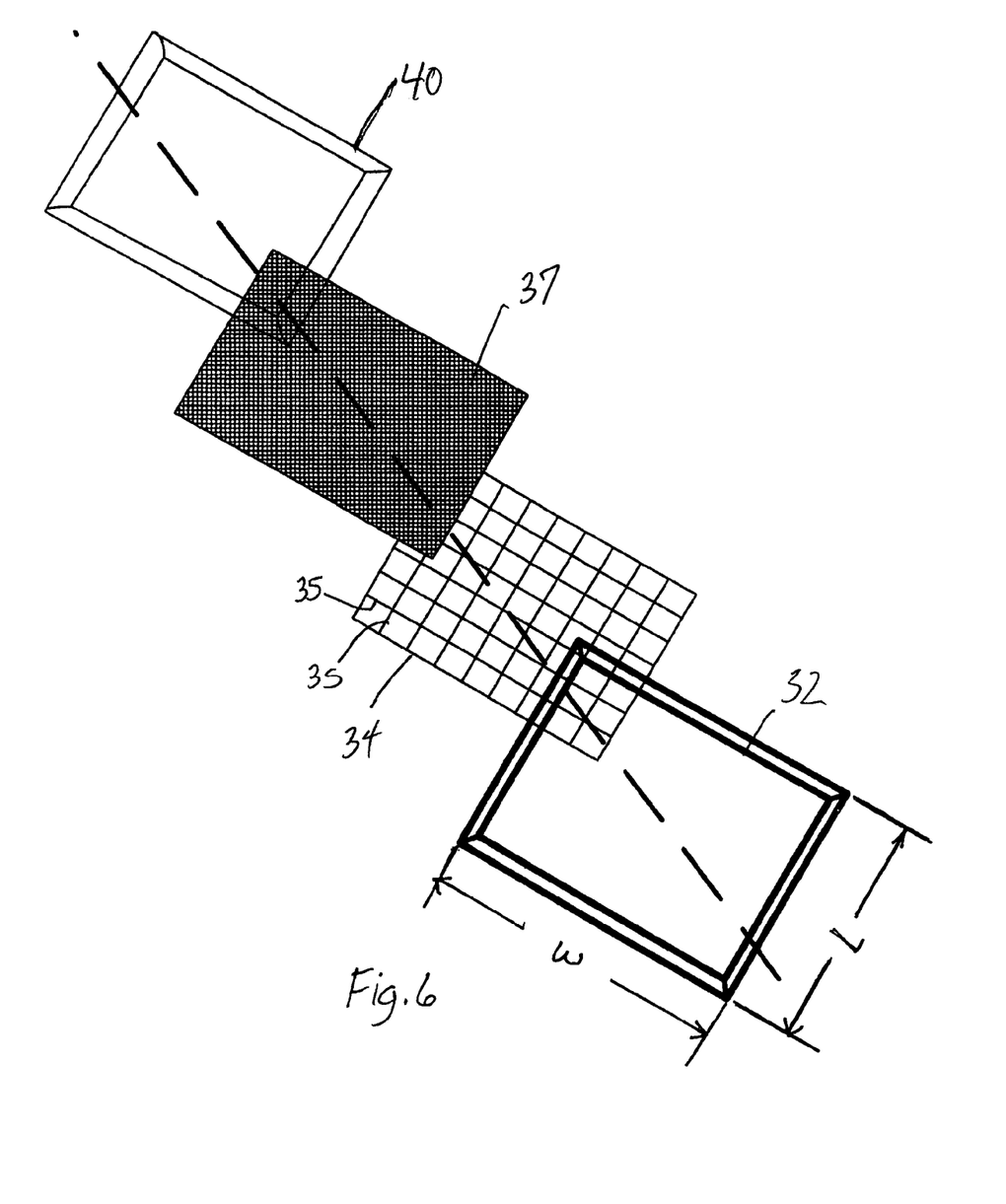
FIG. 6 is an exploded view or illustration of a tray for carrying air treatment material shown in FIGS. 3-4.

Referring to FIG. 6, the trays 30, in the illustrated embodiment, have a frame 32 that defines the length and width of the tray. The frame 32 is attached to the frame 20 of the exhaust treatment member 10 (as shown in FIGS. 3 and 4). Frame 32 can be formed from metal, wood, plastic, or any other suitable material. A support structure 34 is positioned within and attached to frame 32. Support structure 34 includes a plurality of segments 35 that extend across the length and width of the tray. The segments 35, in the illustrated embodiment, are formed from wire and attached to each other at the intersection points to form a mesh-type structure. Alternatively, the support structure 34 is formed from wood, plastic, or other suitable materials. Alternatively still, the segments 35 are not connected to each other, but to the frame 32 of the tray 30.

Liner material 37, is a porous material, such as geotextile material, which is placed onto the support structure 34. A layer of air treatment material 40 is then placed onto the trays 30. In one embodiment, the air treatment material 40 is a mixture of biodegradable materials, such as compost and wood chips, although other similar materials may be used. Although shown as a collective mass in FIG. 6, it should be understood that air treatment material 40 can be freely and loosely distributed within the trays 30. The liner material 37 supports the layer of air treatment material 40 and is porous enough to allow moisture to flow through the liner material, but also supports the layer of air treatment material. Importantly, the liner material 37 allows the microorganisms active in the air treatment material to migrate through the liner material and position themselves on an opposing side of the liner material from the air treatment material 40. Thus, referring again to FIG. 5, as air passes through the pathway 18 of exhaust treatment member 10, more of the air is subjected to interaction with the microorganisms to reduce the concentration of unwanted gases, including hydrogen sulfide and ammonia. For example, as exhaust air travels through segment A microorganisms from the tray 30 located directly above segment A interact with the exhaust air. Similarly, as exhaust air moves through segment B, microorganisms from the trays 30 above and below segment B likewise interact with the exhaust air.

Alternatively, the trays 30 can have a number of different forms without departing from the scope of the invention. For example, the trays 30 can be formed from a five sided box (not shown) having a plurality of apertures formed into a bottom surface of the box and a liner material positioned with the box. Liner material of the type described above may be positioned within the five-sided box to hold the air treatment material, if necessary. As another example, the trays 30 can have a frame to define the length and width with liner material attached to the frame to define a bottom of the tray (not shown). Further, while the illustrated embodiment depicts trays 30 that are attached to the frame 20 of the exhaust treatment member (as shown in FIGS. 3 and 4), alternatively the trays 30 are removably positioned within the exhaust treatment member 10 to allow for maintenance and replacement of the biodegradable material. For example, the trays 30 may be slidably removable from the exhaust treatment member 10.

In the illustrated embodiment, the exhaust treatment member 10 is eight feet wide and eight feet in length. The trays 30 have a width of eight feet and a length of six feet, thereby leaving a two feet by eight feet pathway at the end of each tray for air to reverse course. The exhaust treatment member 10 has a height of eight feet with five trays 30 generally evenly spaced within the exhaust treatment member. These measurements are given for illustrative purposes only. The exhaust treatment member 10 and trays 30 may be sized to properly treat the exhaust air depending upon the output capabilities of the exhaust fan. Thus, the exhaust treatment member 10 and trays 30 may be sized differently without departing from the scope of the invention. As an example, in an alternative embodiment (not shown), to accommodate an exhaust fan with increased flow, the exhaust treatment member 10 has a larger number of trays 30 and therefore the height of the exhaust treatment member is increased. In another alternative embodiment, exhaust treatment member 10 has an extended length, and the corresponding trays 30 are similarly lengthened within the exhaust treatment member. It has been found that increasing the length of trays and, by extension, the overall length of the exhaust treatment member 10 is an effective way to improve the air treatment capabilities of the exhaust treatment member. In still another embodiment, an exhaust fan with smaller total air flow could use a smaller exhaust treatment member 10, including a smaller width and/or length and correspondingly smaller trays 30 or a reduced number of trays and a correspondingly reduced height.

Figure 7:
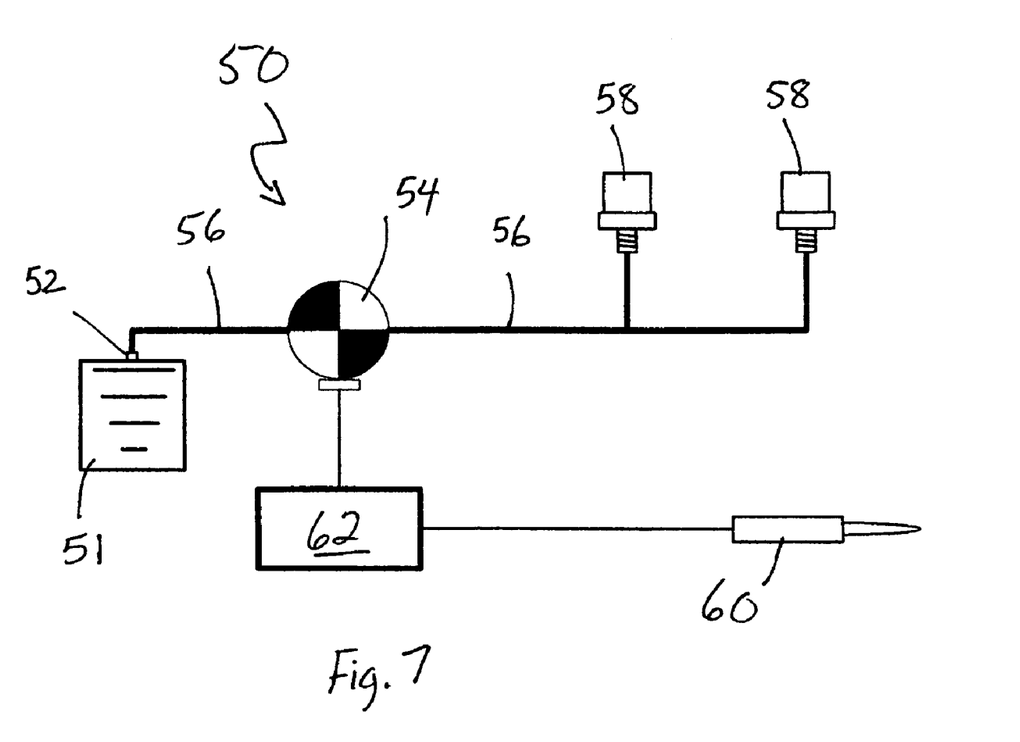
FIG. 7 is a schematic illustration of an irrigation system for the exhaust treatment member of FIG. 1.

Referring to FIGS. 3, 4, and 7, exhaust treatment member 10 includes an irrigation system 50 for measuring the moisture level of the biodegradable material 40 and providing moisture to the biodegradable material to maintain the moisture within a desired moisture level to maintain acceptable microorganism activity. Irrigation system 50 includes an inlet 52 for connection to a moisture source 51. In one embodiment, the moisture source is a pressurized water source 51. Alternatively, the moisture source 51 can be an unpressurized water source. Alternatively still, the moisture source 51 can include substances other than water. For example, chemicals may be added to the moisture source 51 to treat the biodegradable material.

Moisture is transmitted from the moisture source 51 to a flow control member 54 through a conduit 56. Flow control member 54 controls the flow of moisture through the irrigation system, including blocking flow, if necessary. In one embodiment, the flow control member is a valve. More particularly, flow control member, in one embodiment, is a solenoid valve. The valve can be an on/off valve or alternatively, it can be a metering valve for controlling the amount of flow within the moisture system. Alternatively, the flow control member 54 is a pump for drawing moisture from an unpressurized moisture source 51. Conduit 56 can be pipes or hoses suitable for transporting water in the irrigation system 50.

The irrigation system 50 also includes, in one embodiment, a plurality of moisture distribution members 58 positioned in proximity to the plurality of trays 30 within the exhaust treatment member 10 to distribute moisture to the biodegradable material 40. In the illustrated embodiment, the moisture distribution member 58 is a sprinkler head positioned above the tray 30, although other types and arrangements of moisture distribution members may be used. In the illustrated embodiment, two moisture distribution members 58 are positioned over each of the plurality of trays 30. The number of moisture distribution members 58 may vary depending on the size of the trays and the amount of area to which each of the moisture distribution members can provide moisture. Each of the moisture distribution members 58 is attached to the flow control member 54 through a plurality of conduits 56.

The irrigation system 50 also includes a moisture sensor 60 positioned within the exhaust treatment member 10 to sense the moisture level of the biodegradable material 40. In one embodiment, the sensor 60 is positioned within one of the trays 30 that define a portion of segment B of pathway 18 (shown in FIG. 5). Alternatively, the moisture sensor 60 can be positioned anywhere within the exhaust treatment member 10. Alternatively still, the irrigation system 50 can include a plurality of moisture sensors 60 positioned within the exhaust treatment member 10.

The moisture sensor 60, in one embodiment, is connected to a controller 62, which is adapted to interact with the moisture sensor to determine the moisture content of the air treatment material 40. The controller 62 is, in one embodiment, an electronic controller that receives an electric signal from the moisture sensor 60. Controller 62 can be any type of known electronic controller, including a programmable logic controller, a programmable logic array, or similar types of controllers or electronic devices. Controller 62 sends an electrical signal to flow control member 54 to activate the flow control member to supply moisture through the plurality of conduits 56 to the moisture distribution members 58.

The current invention provides a number of advantages. Exhaust air is treated without incurring significant head loss on the exhaust fan. The current invention reduces the problems associated with traditional biofilter fields, including a need for a sloped area and a relatively large amount of land for the biofilter field. In addition, the enclosed structure reduces the effects of channeling of biodegradable material. The irrigation system provides an effective way to keep the biodegradable material within a desired range of moisture content to improve the performance of the microorganisms. In addition, such a system is easily adapted to existing structures.

Those skilled in the art will appreciate that modifications can be made to the illustrative embodiments without departing from the scope of the invention.

What is claimed:

1. An apparatus for treating air exhausted from an agricultural building to reduce the concentration of unwanted gases in the air, comprising:
    an enclosed housing, having:
        an inlet for receiving air exhausted from an agricultural building;
        a discharge outlet;
        a plurality of generally horizontally-oriented trays positioned generally parallel to one another in a vertically spaced-apart arrangement within the housing to define an air pathway through the housing with a plurality of generally parallel horizontal segments positioned in an alignment with turns between the parallel segments to direct air from one horizontal segment to the next and upwardly to the discharge outlet;
        porous liners within the trays,
        biofilter air treatment material positioned on the porous liners in the plurality of trays so that agricultural building air is exposed to the air treatment material as it moves through the pathway and through the trays; and
        mounts for removably supporting the trays within the housing enabling the removal of the trays and replacement of the biofilter air treatment material,
    an irrigation system, having:
        an irrigation inlet for connection to a moisture source;
        at least one moisture distribution member for irrigating the biofilter air treatment material;
        at least one moisture sensing device for monitoring the moisture level of the biofilter air treatment material and providing control signals as a function of the moisture level;
        a conduit from the irrigation inlet to the at least one moisture distribution member; and
        a flow control member connected to the moisture sensing device for controlling the flow of moisture from the irrigation inlet to the at least one moisture distribution device in response to the control signals, to maintain a moisture level in the biofilter air treatment material.

* * * * *